United States Patent [19]

Ding et al.

[11] Patent Number: 5,254,726
[45] Date of Patent: Oct. 19, 1993

[54] NO-CARRIER-ADDED (NCA) ARYL (18F) FLUORIDES VIA THE NUCLEOPHILIC AROMATIC SUBSTITUTION OF ELECTRON RICH AROMATIC RINGS

[75] Inventors: Yu-Shin Ding, Central Islip; Joanna S. Fowler, Bellport; Alfred P. Wolf, Setauket, all of N.Y.

[73] Assignee: The United States of America as represented by the Department of Energy, Washington, D.C.

[21] Appl. No.: 711,684

[22] Filed: Jun. 7, 1991

[51] Int. Cl.$^5$ .................. C07C 229/42; C07C 213/08; C07C 47/52
[52] U.S. Cl. ...................... 562/445; 562/446; 564/360; 568/433; 568/437
[58] Field of Search ............... 562/445, 446; 564/360; 568/433, 437

[56] References Cited

PUBLICATIONS

Ding, et al. J. Flourine Chem. 48 (Jun. 8, 1990) 189-205.
Fowler et al., Annual Reports in Medicinal Chemistry, 24, 277, Allen (Ed.) Academic Press Inc., N.Y. (1989).
Jacobson, JAMA, 259, 2438 (1988).
Eisenhofer et al., J. Clin. Sci., 76, 171 (1989).
Rose et al., J. Clin. Invest., 76, 1740 (1985).
Fowler et al., J. Med. Chem., 17, 246 (1974).
Fowler et al., Radiopharmaceuticals, 196, Subramanian et al. (Eds.), The Society of Nuclear Medicine, Inc., N.Y. (1975).
Kilbourn, "Fluorine-18 Labeling of Radiopharmaceuticals", Nuclear Science Series, NAS-NS-3203, 1-149, National Academy Press, Wash., D.C. (1990).
Mislankar et al., J. Med. Chem., 31, 362 (1988).
Haka et al., J. Nucl. Med., 30, 767 (1989).
Wieland et al., J. Med. Chem., 33, 956 (1990).
Rosenspire et al., Nucl. Med. Biol., 16, 735 (1989).
Schwaiger et al., Circulation, 82, 457 (1990).
Kopin, Circulation, 82, 646, (Ed. Viewpoint) (1990).
Kirk et al., J. Med. Chem., 22, 1493 (1979).
Chiueh et al., J. Pharmacol. Exp. Ther., 225, 529 (1983).
Kirk, J. Org. Chem., 41, 2373 (1976).

Eisenhofer et al., J. Pharmacol. Exp. Ther., 248, 419 (1988).
Goldstein et al., Circulation, 82, 359 (1990).
Cacace et al., J. Label Cmpds. Radiopharm., 18, 1721 (1981).
Attina et al., J. Chem. Soc. Chem. Commun., 108, (1983).
Attina et al., J. Label Cmpds. Radiopharm., 20, 50 (1983).
Angelini et al., J. Fluorine Chem., 27, 177 (1985).
Shiue et al., J. Label. Cmpds. Radiopharm., 21, 533 (1984).
Lemaire et al., Int. J. Appl. Radiat. Isot., 38, 1033 (1987).
(List continued on next page.)

Primary Examiner—José G. Dees
Assistant Examiner—Joseph M. Conrad, III
Attorney, Agent, or Firm—Margaret C. Bogosian; Thomas G. Anderson; William R. Moser

[57] ABSTRACT

A method for synthesizing no-carrier-added (NCA) aryl [$^{18}$F] fluoride substituted aromatic aldehyde compositions bearing an electron donating group is described. The method of the present invention includes the step of reacting aromatic nitro aldehydes having a suitably protected hydroxyl substitutent on an electron rich ring. The reaction is carried out by nucleophilic aromatic substitution with a no-carrier-added (NCA) [$^{18}$F]fluoride ion. The method of the present invention can be used to synthesize various no-carrier-added aryl [$^{18}$F]fluoride compositions, including 6-[$^{18}$F]fluoro-L-DOPA, 2-[$^{18}$F]fluorotyrosine, 6-[$^{18}$F]fluoronorepinephrine, and 6-[$^{18}$F]fluorodopamine. In those instances when a racemic mixture of enantiomers is produced by the present invention, such as in the synthesis of 6-[$^{18}$F]fluoronorepinephrine, a preferred method also includes resolution of the racemic mixture on a chiral HPLC column. This procedure results in a high yield of enantiomerically pure [$^{18}$F] labeled isomers, for example [−]-6-[$^{18}$F]fluoronorepinephrine and [+]-6-[$^{18}$F]fluoronorepinephrine.

3 Claims, 8 Drawing Sheets

PUBLICATIONS

Haka et al., *J. Label. Cmpds. Radiopharm.*, 27, 823 (1989).
Schuster et al., *J. Org. Chem.*, 53, 5819 (1988).
Suryan et al., *J. Am. Chem. Soc.*, 111, 1423 (1989).
Oguri et al., *Chem. Pharm. Bull.*, 26, 803 (1978).
Antoni et al., *Acta. Chem. Scan. B*, 40, 152 (1986).
Carlson et al., *J. Org. Chem.*, 36, 2319 (1971).
Gadekar et al., *J. Hetero. Chem.*, 129 (1968).
Bhatt et al., *Synthesis*, 249, (1968).
Cole et al., *Aust. J. Chem.*, 33, 675 (1980).
Matthews et al., *Aust. J. Chem.*, 41, 1697 (1988).
Warasaka et al., *Chem. Lett.*, 2073 (1987).
Ohta et al., *Tetrahedron*, 45, 5469 (1989).
Waldermann, *Tetrahedron Lett.*, 30, 3057 (1989).
Wang et al., *Tetrahedron Lett.*, 30, 1917 (1989).
Effenberger et al., *Tetrahedron Lett.*, 31, 1249 (1990).
Maeda et al., *Appl. Radiat. Isot.*, 41, 463 (1990).
Levin et al., *J. Biol. Chem.*, 235, 2080 (1960).
Goldstein et al., *J. Biol. Chem.*, 237, 1898 (1962).
Salomaa et al., *Acta. Chem. Scand.*, 15, 871 (1961).
Matthaei et al., *Naunyn-Schmiedeberg's Arch. Pharmacol.*, 337, 621 (1988).
Johnstone et al., *Tetrahedron*, 35, 2169 (1979).
Dewey et al., *Synapse*, 5, 213 (1990).
Plenevaux et al. Appl. Radiat. Isot. 42(2), 121-7, 1991.

Scheme 1.

Scheme II.

NO-CARRIER-ADDED (NCA) ARYL (18F) FLUORIDES VIA THE NUCLEOPHILIC AROMATIC SUBSTITUTION OF ELECTRON RICH AROMATIC RINGS

The U.S. Government has rights in this invention pursuant to Contract Number DE-AC02-76CH00016, between the U.S. Department of Energy and Associated Universities Inc.

BACKGROUND OF THE INVENTION

1. Field of the Invention

This invention relates to synthesis of no-carrier-added (NCA) aryl [$^{18}$F]fluorides by utilizing nucleophilic aromatic substitution of aromatic rings containing electron donating groups in addition to electron withdrawing and leaving groups. More specifically, this invention has been applied to the synthesis of high specific activity (+) and (−)-6-[$^{18}$F]fluoronorepinephrine by the nucleophilic aromatic substitution reaction, and this compound has been applied to study baboon heart metabolism in vivo using positron emission tomography (PET).

2. Background of the Related Art

Positron emission tomography (PET) is an in vivo imaging modality which measures the spatial and temporal distribution of positron emitter labeled compounds and their labeled metabolities in a volume element of living tissue; for example see: Fowler et al., in *Annual Reports In Medicinal Chemistry*, 24, 277, Allen (Ed.), Academic Press Inc., New York (1989). Although the heart has been extensively studied with PET, it has been examined mainly from the perspective of assessing perfusion and substrate metabolism; see, for example Jacobson, *JAMA*, 259, 2438 (1988). However, the neuronal integrity of the heart is also important in assessing cardiac physiology and pathophysiology; see, Eisenhofer et al., *J. Clin. Sci.*, 76, 171 (1989); and Rose et al., *J. Clin. Invest.*, 76, 1740 (1985). There also has been an interest in probing this function in vivo by using external imaging, beginning with the synthesis of [$^{11}$C]norepinephrine in the early 1970's, as reported by Fowler et al., *J. Med. Chem.*, 17, 246 (1974); and Fowler et al., *Radiopharmaceuticals*, 196, Subramanian et al. (Eds.), The Society of Nuclear Medicine, Inc., New York (1975).

Fluorine-18, because of its ready availability and relatively long half life and low positron energy, is a very attractive nuclide for PET studies. However, because of the inherent difficulties in the formation of carbon-fluorine bonds, its incorporation into organic molecules and labeling with fluorine-18 remains a challenge, see Kilbourn, "Fluorine-18 Labeling of Radiopharmaceuticals", *Nuclear Science Series, NAS-NS*-3203, 1–149, National Academy Press, Washington, D.C. (1990). Prior to the present invention, the only methods so far described for introducing F-18 into an aromatic ring bearing the catecholamine moiety require the use of low specific activity electrophilic fluorination reagents derived from F-18 elemental fluorine.

Recently, interest in studies related to the neuronal integrity of the heart has intensified with the development of [$^{18}$F]fluorometaraminol reported by Mislankar et al, *J. Med. Chem.*, 31, 362 (1988), and [$^{11}$C]m-hydroxyephedrine reported by Haka et al., *J. Nucl. Med.*, 30, 767 (1989). Both compounds are metabolically stable, false neurotransmitters for norepinephrine. These tracers share the same uptake and storage mechanisms as norepinephrine and provide excellent images of the neuronal distribution in the dog heart, as reported by Wieland et al., *J. Med. Chem.*, 33, 956 (1990), and by Rosenspire et al. *Nucl. Med. Biol.*, 16, 735 (1989); and in the human heart, as reported by Schwaiger et al., *Circulation*, 82, 457 (1990), and Kopin, *Circulation*, 82, 646, (Ed. Viewpoint) (1990). Ring-fluorinated catecholamines such as 6-fluoronorepinephrine synthesized by Kirk et al., *J. Med. Chem.*, 22, 1493 (1979) and Chiueh et al., *J. Pharmacol. Exp. Ther.*, 225, 529 (1983); and 6-fluorodopamine synthesized by Kirk, *J. Org. Chem.*, 41, 2373 (1976), and Eisenhofer et al., *J. Pharmacol. Exp. Ther.*, 248, 419 (1988), have been shown to share the same presynaptic mechanisms for the uptake, storage, and synthesis as the parent molecules. Recently 6-[$^{18}$F]fluorodopamine has been synthesized by electrophilic fluorination and used in PET studies of the canine heart, as reported by Goldstein et al., *Circulation*, 82, 359 (1990).

In spite of the fact that both [$^{18}$F]fluorometaraminol and [$^{18}$F]dopamine display binding properties appropriate to their use in PET studies of myocardial innervation, their vasoactivity results in hemodynamic effects when these tracers are administered in vivo, thus limiting their application in humans, see: Goldstein et al. (1990), supra; and Mislankar et al. (1988), supra. Clearly, a route to high specific activity $^{18}$F-labeled catecholamines is needed so that the full potential of this class of compounds as neuronal imaging tracers can be objectively assessed. For these reasons, the inventors have examined the feasibility of preparing $^{18}$F-labeled catecholamines in high specific activity using [$^{18}$F]fluoride and nucleophilic aromatic substitution.

Nucleophilic aromatic substitution by fluoride ion has become one of the most useful labeling techniques utilizing fluorine-18, a positron emitter with a 110 minute half life. The mechanism and conditions necessary for successful substitution were the subject of a series of papers, Cacace et al., *J. Label. Cmpds. Radiophram.*, 18, 1721 (1981); Attina et al. *J. Chem. Soc. Chem. Commun.*, 108 (1983); Attina et al., *J. Label. Cmpds. Radiopharm.*, 20, 501 (1983); and Angelini et al., *J. Fluorine Chem.*, 27, 177 (1985). These techniques now have widespread application in their original or in their modified form as reported by Shiue et al., *J. Label. Cmps. Radiopharm.*, 21, 533 (1984); Lemaire et al., *Int. J. Appl. Radiat. Isot.*, 38, 1033 (1987); and Haka et al., *J. Label. Cmpds. Radiopharm.*, 27, 823 (1989). The leaving group in the substitution reaction on an aromatic ring is usually nitro or -$^{+}$NMe$_3$ and the necessary electron withdrawing group to effect the reaction can be RCO, CN, NO$_2$ etc. There are, however, numerous important radiopharmaceuticals with electron donating substituents, in addition to the electron withdrawing substituents, which can make the substitution reaction proceed in low yield or be wholly ineffective. A few of such multifunctional aromatic compounds include fluorine-18 labeled 6-fluoro-L-DOPA, 2-fluorotyrosine, 6-fluoronorepinephrine, and 6-fluoro-metaraminol. Prior to the present invention, the only known practical synthetic route for a number of these molecules involved the use of the electrophilic fluorinating reagents, either fluorine-18 labeled elemental fluorine, or acetylhypofluorite. The use of these two reagents results in low specific activity, and direct fluorination usually produces a mixture of fluorinated products.

DETAILED DESCRIPTION OF THE INVENTION

Figure 1:
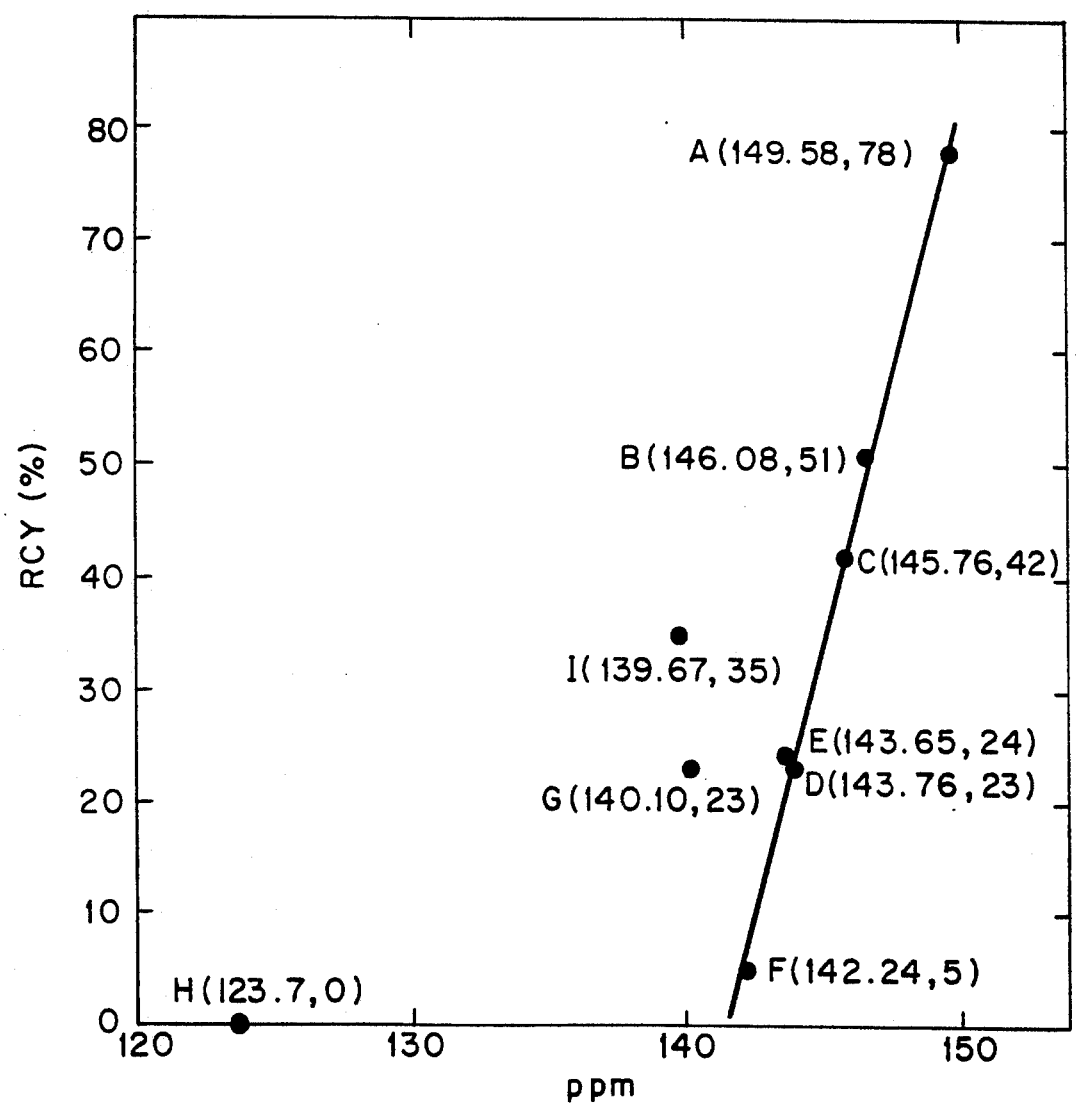
FIG. 1 is a graph showing the correlation between the $^{13}C$ chemical shift of the reaction center and the radiochemical yield.

The present invention achieves a significant improvement over the limitations inherent in the prior methods by providing a method for synthesizing no-carrier-added (NCA) aryl [$^{18}F$] fluoride substituted aromatic aldehyde compositions bearing an electron donating group. The method of the present invention includes the step of reacting aromatic nitro aldehydes having a suitably protected hydroxyl substituent on an electron rich ring. The reaction is carried out by nucleophilic aromatic substitution with a no-carrier added (NCA) [$^{18}F$]fluoride ion. The method of the present invention can be used to synthesize various no-carrier-added aryl [$^{18}F$]fluoride compositions, including 6-[$^{18}F$]fluoro-L-DOPA, 2-[$^{18}F$]fluorotyrosine, 6-[$^{18}F$]fluoronorepinephrine, and 6-[$^{18}F$]fluorodopamine. In the method of the present invention, when 6-[$^{18}F$]fluoro-L-DOPA is synthesized, preferably, the synthesis also includes the steps of hydride reduction, bromination, alkylation and deprotection. In one preferred embodiment, an electron donating group of the aryl [$^{18}F$]fluoride substituted aromatic aldehyde includes a catechol moiety.

In those instances when a racemic mixture of enantiomers is produced by the method of the present invention, such as in the synthesis of 6-[$^{18}F$]fluoronorepinephrine, a preferred method also includes resolution of the racemic mixture on a chiral HPLC column. This procedure results in a high yield of enantiomerically pure [$^{18}F$] labeled isomers. Such enantiomerically pure [$^{18}F$] labeled isomers, for example when 6-[$^{18}F$]fluoronorepinephrine is resolved, would include [−]-6-[$^{18}F$]fluoronorepinephrine and [+]-6-[$^{18}F$]fluoronorepinephrine.

The method of synthesis in accordance with the present invention results in aryl [$^{18}F$]fluoride substituted aromatic aldehyde compositions bearing an electron donating group on an aromatic ring and having specific activities that are greater than 20 mCi/$\mu$mole up to a theoretical limit in specific activity of about 1,700 Ci/$\mu$mole. The electron donating group can include, in one preferred embodiment, a catechol moiety. Preferably, the aryl [$^{18}F$]fluoride compositions produced by the present invention have a specific activity of from about 500 mCi/$\mu$mole to about 10 Ci/$\mu$mole, and most preferably have a specific activity of about 2 Ci/$\mu$mole to about 5 Ci/$\mu$mole. Under normal processing conditions the no-carrier added (NCA) aryl[$^{18}F$]fluoride substituted aromatic aldehyde compositions produced by the present invention are obtained at a very high specific activity of about 2 Ci/$\mu$mole to about 5 Ci/$\mu$mole which is well suited for the preparation of radiopharmaceuticals for PET studies. However, as understood by those of ordinary skill in the art, if such compositions are desired at the less preferred, lower range of the specific activity, i.e. down to 20 mCi/$\mu$mole or below, which is still a much higher specific activity that can be achieved by the prior art electrophilic displacement reaction, then the reaction mixture can be diluted during the aromatic substitution reaction with [$^{19}F$]fluoride ion in order to achieve these lower specific activities. Thus, the specific activity of the final composition can be adjusted by the addition of a suitable concentration of carrier added [$^{18}F$]/[$^{19}F$]fluoride ion to the substitution reaction. Alternatively, high specific activity compounds made in accordance with this invention can be diluted with cold, i.e., the same, albeit non-radioactive aryl fluoride substituted aromatic compounds to achieve a desired lower specific activity.

The present invention represents the first time that nucleophilic aromatic substitution by [$^{18}F$]fluoride ion has been demonstrated on rings containing electron donating groups in addition to the necessary electron withdrawing and leaving groups. The reaction of [$^{18}F$]− with a series of aromatic nitro aldehydes having protected hydroxyl substituents on the ring is shown in the Examples. The reactivity of the aromatic ring towards nucleophilic substitution to give $^{18}F$-labeled aromatic fluoroaldehyde derivatives is correlated with electron density at the reaction center. $^{13}C$-NMR was used as a sensitive probe for the changes in electron distribution at the ring carbon atoms. Radiochemical yield correlates with ppm values at the reaction center. This methodology has been applied to the synthesis of no-carrier-added (NCA) 6-[$^{18}F$]fluoro-L-DOPA, a compound which has been used to study dopamine metabolism in human brain in vivo using positron emission tomography (PET). The method of the present invention can be extended to the synthesis of other labeled pharmaceuticals with higher specific activities, such as 2-fluorotyrosine for studying in vivo protein metabolism, 6-fluoronorepinephrine and 6-fluorodopamine for studying adrenergic receptors and myocardial innervation.

The considerable importance of the [$^{18}$F]fluoride ion for labeling radiopharmaceuticals and the biomolecules used in PET research lead to using nucleophilic aromatic substitution by [$^{18}$F]fluoride ion as a more general method applicable to aromatic substitution when both electron donating and electron withdrawing substituents are present on the aromatic ring. Accordingly, a series of compounds with hydroxyl groups suitably protected were prepared using no-carrier-added (NCA) $^{18}$F$^-$ as the labeling nucleophile. Also, in another embodiment of this method, the synthesis of 6-[$^{18}$F]fluoro-L-DOPA is shown in the Examples.

This is the first synthesis of a no-carrier-added (NCA) $^{18}$F-labeled catecholamine, 6-[$^{18}$F]fluoronorepinephrine(6-[$^{18}$F]FNE), by utilizing nucleophilic aromatic substitution. The racemic mixture of the present invention was resolved on a chiral HPLC column to obtain pure samples of (−)-6-[$^{18}$F]FNE and (+)6-[$^{18}$F]FNE. Radiochemical yields of 20% at the end of bombardment (EOB) for the racemic mixture (synthesis time 93 min), 6% for each enantiomer (synthesis time 128 min) with a specific activity of 2-5 Ci/μmol at EOB were obtained. Chiral HPLC peak assignment for the resolved enantiomers was achieved by using two independent methods: (1) polarimetric determination, and (2) reaction with dopamine β-hydroxylase. Positron emission tomography (PET) studies with racemic 6-[$^{18}$F]FNE show high uptake and retention in the baboon heart. The Examples demonstrate that nucleophilic aromatic substitution by [$^{18}$F]fluoride ion is applicable to systems having electron-rich aromatic rings, leading to high specific activity radiopharmaceuticals. Furthermore, the suitably protected dihydroxynitrobenzaldehyde may serve as a useful synthetic precursor for the radiosynthesis of other complex $^{18}$F-labeled radiotracers.

This is also the first time that such a racemic mixture was resolved on a chiral HPLC column, and also represents the first time a chiral column was used as a synthetic tool to produce enantiomerically pure $^{18}$F-labeled isomers for PET studies. No other reported method has used an enzymatic reaction to assign the peaks for the resolved enantiomers on chiral HPLC. Most of all, it is the first time that PET studies have been carried out in the baboon heart with a no-carrier-added $^{18}$F-labeled catecholamine.

Studies of the nucleophilic substitution reaction appear to indicate that the hydroxyl protecting group plays an important role in controlling the reactivity of the aromatic ring towards nucleophilic substitution. Table 1 shows the effects which different protecting groups have on this reaction. When there was no electron donating group on the ring, the radiochemical yield for nucleophilic substitution was the highest. When the dihyroxyl groups were protected as 1,3-benzodioxolanes (compound B and C), the yields were still good, but when protected as dialkyl groups D and E), the yields decreased. In the case of only one methoxy group para to the nitro group (compound F), only a 5% yield was obtained. However, a single methoxy ortho to the nitro group (compound G) gave the $^{18}$F-labeled product in a 23% yield. 1,4-Benzodioxan-6-carboxyaldehyde (compound H) was essentially inert to nucleophilic substitution, while compound 1 which has a nitro group para to the formyl group, afforded a 35% yield of product.

TABLE 1

Structural Effects of Various Protecting Groups on Radiochemical Yields in Nucleophillic Substitution with NCA $^{18}$F$^-$

| Compound | Radiochemical Yield (EOB) |
|---|---|
| (A) | 78% |
| (B) | 51% |
| (C) | 42% |
| (D) | 23% |
| (E) | 24% |
| (F) | 5% |
| (G) | 23% |
| (H) | 0% |

TABLE 1-continued

Structural Effects of Various Protecting Groups on Radiochemical Yields in Nucleophillic Substitution with NCA $^{18}$F⁻

| Compound | | Radiochemical Yield (EOB) |
|---|---|---|
| (I) | 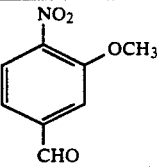 | 35% |

To probe the electron density at the reaction center, an approach suggested by Schuster, et al., *J. Org. Chem.*, 53, 5819 (1988), and Suryan et al., *J. Am. Chem. Soc.*, 111, 1423 (1989) the disclosure of which is incorporated by reference herein, for the electron donating effect on unhindered and crowded anisoles may be applied. The methoxy groups of unhindered anisoles tend to lie in the aromatic plane with an Ar-O-Me bond angle of 117°–118°, a value near that is expected for sp²-hybridized oxygen. This arrangement has the optimum overlap between the oxygen p-type lone pair orbital and the aromatic π system. In crowded anisoles, nonbonded interactions may force the CH₃ of the methoxy group out of the aromatic plane. The hybridization of the oxygen then approaches sp³ and the overlap decreases. As a consequence there will be a lowering of the π-electron densities at the para carbon atoms, a phenomenon which was verified by ¹³C-NMR chemical shift. Since a similar crowding and rehybridization mechanism could explain the relative reactivities of the compounds listed in Table I, the inventors examined their ¹³C-NMR spectra in order to test this hypothesis. ¹³C-NMR analysis was applied to detect experimentally the changes in electron distribution at the ring carbon atoms of a series of aromatic nitroaldehydes with different hydroxyl protecting groups.

FIG. 1 is a graph showing the correlation between the ¹³C chemical shift of the reaction center and the radiochemical yield. As shown in FIG. 1, for the structurally similar compounds A through F, a good correlation between ¹³C chemical shifts and radiochemical yields was obtained by plotting the chemical shifts of the reaction center (where the nitro group is attached) against the corresponding radiochemical yield obtained from Table I. These results show that a downfield chemical shift (larger ppm value) at the reaction center should indicate a lower electron density and therefore result in a higher radiochemical yield for nucleophilic substitution. The fact that three cases (compounds G, H, I) fell off the straight correlation line could be ascribed to the fact that compounds G-I were structurally different from compounds A through F. That is, in the case of compound G, instead of having a meta or para methoxy group relative to the nitro group, it has an ortho methoxy group which, being more hindered, should be less able to donate electrons, thus affording a higher yield than compound F. Compound H was expected to be unreactive to nucleophilic substitution since the reaction center possessed a relatively high electron density indicated by a smaller ppm value in its ¹³C-NMR (26 ppm further upfield than that observed for the corresponding carbon in compound A). A better yield was obtained for compound I than for compound G. As compound I has a NO₂ group para to the formyl group, the higher yield suggests increased reactivity towards nucleophilic substitution due to less steric hindrance.

Figure 2:
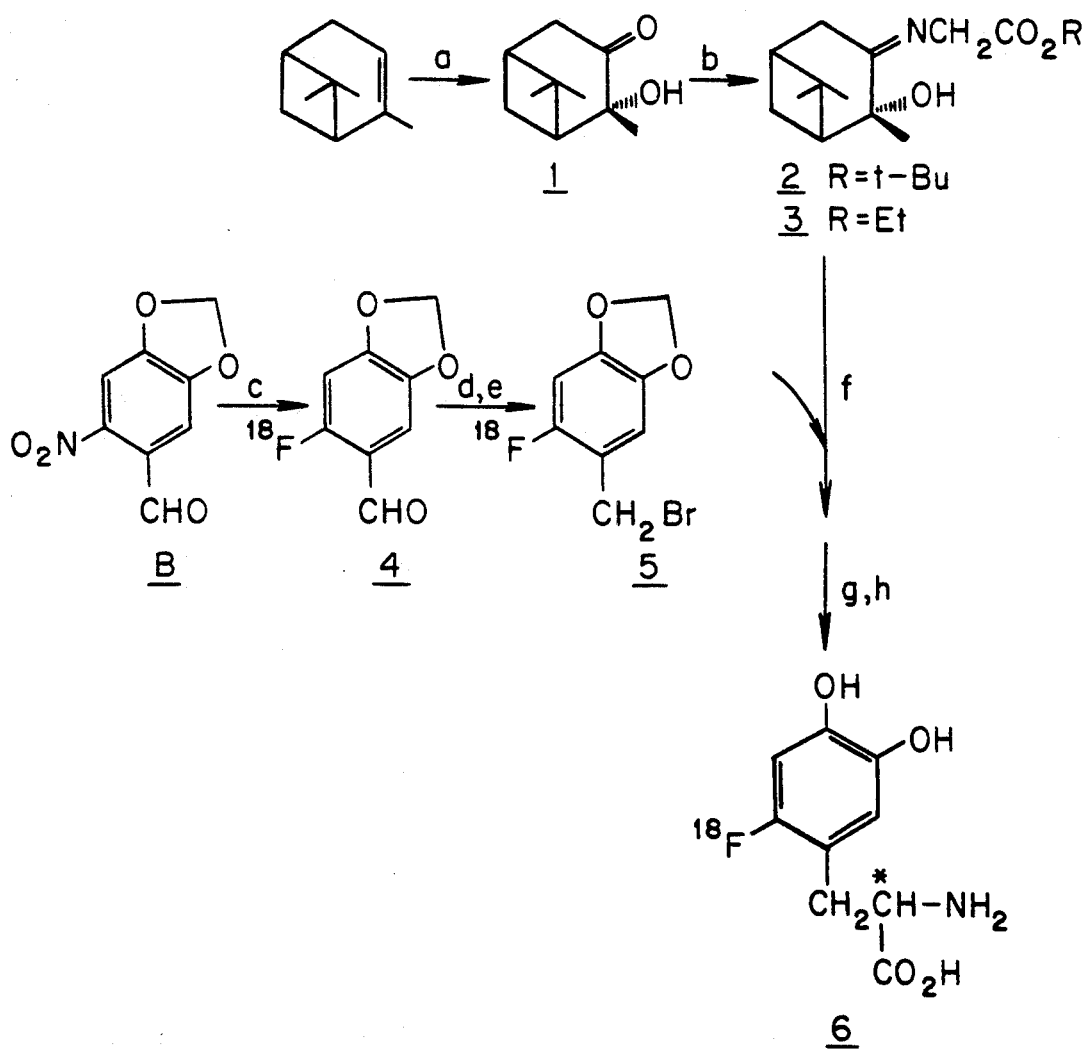
FIG. 2 illustrates the asymmetric synthesis (Scheme I) of NCA 6-[$^{18}F$]Fluoro-L-DOPA(designated as compound 6) in accordance with the present invention. Steps are as follows: a. $KMnO_4$, 90% Acetone/$H_2O$; b. $BF_3.Et_2O$/benzene, $H_2NCH_2CO_2R$; c. $K^{18}F$, Kryptofix 222; d. $LiAlH_4$; e. $SOBr_2$, pyr.; f. LiTMP/THF; g. $NH_2OH$, HCl; h. HPLC.

The identification of the structural requirements for effecting the nucleophilic aromatic substitution reaction in moderate yield holds the promise of the synthesis of useful radiotracers through elaboration of the aldehyde moiety. FIG. 2 illustrates the asymmetric synthesis (Scheme I) of NCA 6-[¹⁸F]Fluoro-L-DOPA(designated as compound 6) in accordance with the present invention. This no-carrier-added radiotracer was prepared from asymmetric alkylation of a chiral synthon, which is generally described by Oguri et al., *Chem. Pharm. Bull.*, 26, 803 (1978) and Antoni et al., *Acta. Chem. Scand. B*, 40, 152 (1986) the disclosure of both of these articles is incorporated by reference herein, glycine ester derivatives 2 or 3, with 6-[¹⁸F]fluoropiperonyl bromide 5 (Scheme 1). The chiral synthon was prepared from chiral ketol 1, described by Carlson et al., *J. Org. Chem.*, 36, 2319 (1971) the disclosure of which is incorporated by reference herein, which was itself derived from (−)-α-pinene and a glycine ester. The ¹⁸F labeled bromide 5 was prepared using nucleophilic displacement of the activated nitro group of 6-nitropiperonal B by NCA ¹⁸F⁻ to yield compound 4, followed by reduction with LiAlH₄ and bromination with SOBr₂. The alkylation was carried out using anhydrous conditions in THF with 2,2,6,6,-tetramethylpiperidyllithium as a base. Upon deprotection, the product was assayed by HPLC and was found to contain 6-[¹⁸F]fluoro-L-DOPA in approximately 12% overall radiochemical yield (EOB). The radiosynthesis involved five steps: 1. displacement by [¹⁸F]⁻, 2. hydride reduction, 3. bromination, 4. alkylation, and 5. hydrolysis.

The synthesis described in Examples 10 through 12 below applies the method of the present invention to the preparation of 6-FNE using (2,2-dimethylbenzodioxolane) compound C which has an aromatic ring bearing a suitably protected catechol as a starting point. 6-FNE (designated as compound 16) is produced in high specific activity and in practical yields for PET studies. Moreover the resolution of the racemic mixture with chiral HPLC proceeds efficiently and in high yields providing for the first time the opportunity to examine the biological behavior of the individual enantiomers of 6-FNE in vivo.

Initial PET studies with racemic 6-[¹⁸F]FNE described in Example 13, show a high uptake and a slow clearance of radioactivity from a baboon heart. On the basis of these PET studies showing a high uptake and slow clearance of 6-[¹⁸F]FNE from the baboon heart, and previous studies showing that racemic 6-fluoronorepinephrine is taken up and stored by adrenergic nerve terminals, as reported by Chiueh et al., *J. Pharmacol. Exp. Ther.*, 225, 529 (1983) the disclosure of which is incorporated by reference herein, it is likely that the image represents neuronal, and perhaps vesicular 6-[¹⁸F]FNE.

It is known that the neuronal uptake of norepinephrine itself is not stereoselective only the levorotatory enantiomer serves as a substrate for the vesicular transporter, see: Matthaei et al., *Naunyn-Schmiedeberg's Arch. Pharmacol.*, 337, 621 (1988) the disclosure of which is incorporated by reference herein. If 6-fluoronorepinephrine exhibits the same stereoselectivity for vesicular storage as norepinephrine itself, PET studies of the individual labeled enantiomers should provide the potential for assessing vesicular storage.

EXAMPLES

I. Materials and Methods

Figure 3:
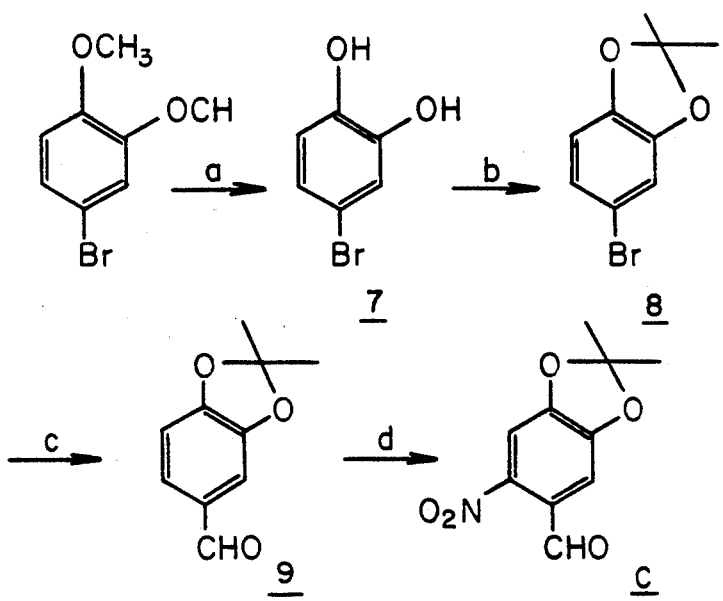
FIG. 3 illustrates the Synthesis (Scheme II) of 3,4-O-isopropylidene-6-Nitro-Benzaldehyde(designated as compound C) in accordance with the present invention. Steps are as follows: a. $BBr_3/CH_2Cl_2$; b. Acetone, PTSA/Benzene c. Mg,DMF/THF; d. $HNO_3$.

Except compound C (see: synthetic Scheme II in FIG. 3), compounds A-I used in the comparative studies were either purchased from Aldrich or prepared by the routine procedure for methylation ($K_2CO_3$/Met-/EtOH), as described by Johnstone et al., *Tetrahedron*, 35, 2169 (1979), or nitration, as described by Gadekar et al., *J. Hetero. Chem.*, 129 (1968) the disclosure of both of these articles is incorporated by reference herein, described for the synthesis of compound C) from the commercially available precursors. $^{13}C$ NMR spectra of aromatic nitroaldehydes were recorded with a Brucker 300 MHz as 0.5M solutions in deuteriochloroform.

(1S)-(−)-α-pinene, 6-nitropiperonal, boron tribromide, glycine ethyl ester, lithium aluminum hydride (1M in diethyl ether) and thionyl bromide were obtained from Aldrich. Glycine t-butyl ester was purchased from Sigma Chemical Company. Hydroxylamine (free base) was obtained from Southwestern Analytic Chemicals, Inc. 6-Fluoronorepinephrine was purchased from RBI (Research Biochemicals Inc.). Dopamine and dopamine β-hydroxylase was obtained from the Sigma Chemical Co. $^1H$ NMR spectra were also recorded with a Brucker 300 MHz in $CDCl_3$ as a solvent using TMS as internal reference. Mass spectra were recorded with a Finnegan-Mat GC-MS 5100 mass spectrometer using electron impact ionization at 70 eV. HPLC analyses were carried out with a Perkin-Elmer liquid chromatograph equipped with a radioactivity monitor and UV detector. Optical rotation analysis was performed by Rudolph Instruments, Inc.

EXAMPLE 1

Nucleophilic Aromatic Fluorination with NCA $^{18}F^-$

NCA $^{18}F^-$ ions for displacement were prepared by dissolving 4 mg of $K_2CO_3$ and 20 mg of Kryptofix 222 in aqueous $H^{18}F$ solution, prepared from the $^{18}O(p,n)^{18}F$ reaction in a small volume $H_2^{18}O$ target. The aqueous solution was evaporated in a Pyrex vessel at 120° while purging with a slow stream of nitrogen, and then coevaporated to dryness with acetonitrile. The comparative studies with compounds having different protecting groups were carried out using 2 mCi $^{18}F^-$ in each case.

A solution of the aromatic substrate (0.051 mmol) in 0.3 mL of dry DMSO was added to $K^{18}F$/Kryptofix 222. The mixture was stirred at 120° for 10 minutes, quenched by adding water (3 mL) and extracted with $CH_2Cl_2$ (2×2 mL). The $CH_2Cl_2$ extracts were dried by passing through a $K_2CO_3$ column. The activities of the aqueous and organic layers were then measured in a scintillation counter (Picker Nuclear Inc.) to determine the fraction of the $^{18}F^-$ activity incorporated into the organic products. The radiochemical purity of the $^{18}F$-labeled product(s) from the organic layer was assayed by thin layer chromatography (30% ethyl acetate/hexane) and radio HPLC (Berthold Radioactivity Monitor, Model LB 503 flow scintillation counter). The HPLC analyses were performed on a phenomenex column (Ultremex), 5 sil, 250×4.6 mm), eluting with a mixture of hexane:$CH_2Cl_2$:i-PrOH=80:20:0.5. In each case, a single product was obtained (radiochemical purity was greater than 99%).

EXAMPLE 2

Synthesis of (+)-2-Hydroxypinan-3-one(1) and [(+)-2-Hydroxy-pinanyl-3-idene]glycine t-butyl ester (2) or ethyl ester (3)

Compounds (1), (2), and (3) were synthesized according to Oguri et al. (1978) supra, and Carlson et al. (1971) supra, the disclosures of which are incorporated by reference herein. Compound (1) was purified by distillation to give a colorless oil, $bp_{15}$ 119°–120° C., $^1H$-NMR ($CDCl_3$) 2.62–1.65 (m, 7H), 1.38 (s, 3H, $CH_3$), 1.36 (s, 3H, $CH_3$), 0.88 (s, 3H, $CH_3$). Compounds (2) and (3) were purified by column chromatography. $^1H$-NMR ($CDCl_3$) of 2, δ4.23 (q, 2H), 4.16 (d, 2H), 2.70–1.55 (m, 7H), 1.52 (s, 3H), 1.33 (s, 3H), 1.30 (t, 3H), 0.87 (s, 3H). $^1H$-NMR ($CDCl_3$) of 3, δ4.08 (d, 2H), 2.70–1.55 (m, 7H), 1.52 (s, 3H), 1.48 (s, 3H), 1.33 (s, 3H), 0.87 (s, 3H).

EXAMPLE 3

Synthesis of NCA 6-[$^{18}F$]Piperonyl Bromide (5)

The $K^{18}F$/kryptofix 222 was prepared as described in Example 1. A solution of p-nitropiperonal 4 (10 mg) in 0.3 mL of dry DMSO was added to the dried $K^{18}F$/kryptofix 222. The mixture was stirred at 120° for 5 minutes, cooled in an ice bath, and then 0.2 mL of 1M lithium aluminum hydride in diethyl ether was added. The resulting mixture was stirred at room temperature for 10 minutes, cooled in an ice bath, and then 1 mL of saturated $NaCl_{(aq)}$ was added. After the mixture was extracted with ether (3×1 mL), the combined extracts were dried by passing through $K_2CO_3$ and concentrated to give approximately 1 mL solution. Pyridine (0.04 mL) and thionyl bromide (0.04 mL) were added sequentially. The reaction mixture was stirred at room temperature for 5 minutes, then diluted with 1 mL of ice water and extracted with ether (2×1 mL). The combined ether layers were dried by passing through $K_2CO_3$. The solvent was then evaporated and the residue taken up in 0.3 mL of dry THF. The solution of 6-[$^{18}F$]piperonyl bromide 5 was analyzed by thin layer chromatography (silica, 7:3 hexane:ethyl acetate; 6-[$^{18}F$]piperonyl alcohol $R_F$=0.24, 6-[$^{18}F$]piperonyl bromide $R_F$=0.68). The labeled bromide was used for the alkylation step without further purification.

EXAMPLE 4

Alkylation of the Schiff Base (2) with 6-[$^{18}F$]Piperonyl Bromide (5)

[(+)-2-Hydroxypipanyl-3-idene]glycine ethyl ester 3 (25–50 mg, 9.8–19.7×10$^{-5}$ mol) and 2,2,6,6-tetramethyl-piperidyl-lithium (2.4–4.9×10$^{-4}$ mol) in THF, total volume 0.6–0.8 mL, was cooled to −78° C. with dry ice/acetone. The solution of crude 6-[$^{18}F$]piperonyl bromide 5 in THF was then added to the mixture of the Schiff base anion freshly prepared as described in Example 3. The resulting mixture was stirred for 15 minutes at 78° C., and the solution of crude product was analyzed by TLC (silica gel, 6:4 hexane:ethyl acetate). The alkylation product was deprotected without isolation.

EXAMPLE 5

Synthesis of 6-[$^{18}F$]Fluoro-L-DOPA (6)

The alkylation reaction described in Example 4 was quenched at −78° C. by adding 0.6M hydroxylamine acetate in 70% aqueous ethanol (0.4 mL), followed by addition of concentrated HCl (3 mL) and then heated in a closed vessel (fitted with a 0.2 mm tube to release pressure) at 125° C. for 30 min.

Analytical HPLC of the product was carried out on a Phenomenex NH2 column (100×4.6 mm, particle size 5 um) under the following conditions: flow 1.0 mL/min, $CH_3CN$:0.01M $KH_2PO_4$=65:35, pH 3.60, 254 nm; or on a Phenomenex ODS column (250×4.6 mm) eluting with 0.1% $CH_3COOH$ (1.8 mL/min, 280 nm). The radioactive peak corresponding to 6-[$^{18}F$]fluoroDOPA had the same retention time as an authentic, inactive sample provided by Dr. Kenneth Kirk at the National Institute of Health (time corrected for time delay between mass detector and radiodetector). This reaction sequence was also carried out with 3,4-O-isopropylidine-6-nitrobenzaldehyde (C). Deprotection of this compound was effected.

EXAMPLE 6

Synthesis of 3,4-dihydroxybromobenzene (7)

4-Bromoveratrole (30 g, 0.138 mol) was placed in a three-neck reaction flask and cooled in an ice bath. Boron tribromide, as described Bhatt et al., *Synthesis*, 249, (1968) the description of which is incorporated by reference herein, (1.0M in $CH_2Cl_2$, 0.2 mol) was slowly introduced through a dropping funnel. After the addition was complete, the reaction mixture was refluxed overnight (20 h). The solution was chilled to 0° C. and water was added slowly. The residue was hydrolyzed with a minimum amount of 10% $NaOH_{(aq)}$. The resulting solution was acidified with hydrochloric acid and extracted with ether. The extracts were washed with $H_2O$ and brine, then dried over anhydrous $MgSO_4$ and concentrated in vacuo to afford compound 7 (24 g, 92%). The product was used in the next step without purification (only one spot by TLC). $^1$H-NMR ($CDCl_3$) $\delta$7.02 (d, 1H, $J_{meta}$=2.26 Hz), 6.92 (dd, $J_{ortho}$=8.45 Hz, $J_{meta}$=2.26 Hz), 6.74 (d, $J_{ortho}$=8.45 Hz).

EXAMPLE 7

Synthesis of 3,4-O-isopropylidenebromobenzene (8)

Catechol 7 (10 g), acetone (30 mL, excess), p-toluenesulfonic acid (150 mg) and benzene (30 mL) were heated under reflux for 72 h, in accordance with Cole et al., *Aust. J. Chem.*, 33 675 (1980) the disclosure of which is incorporated by reference herein. The condensed azeotrope was percolated through a bed of molecular sieves (Linde, 1/16" pellets) before returning solvent/acetone to the flask. The solvent was removed using a rotary evaporator and the reaction mixture was purified by column chromatography ($CHCl_3$/hexane) to afford compound 8 (3.0 g, 25%). The starting material (7.0 g) was recovered (by eluting with ethyl acetate/hexane) and could be reused. $^1$H-NMR ($CDCl_3$) $\delta$6.90 (dd, 1H, $J_{ortho}$=8.12 Hz, $J_{meta}$=1.98 Hz), 6.86 (d, 1H, $J_{meta}$=1.98 Hz), 6.60 (d, 1H, $J_{ortho}$=8.12 Hz), 1.67 (s, 6H).

EXAMPLE 8

Synthesis of 3,4-O-isopropylidenebenzaldehyde (9)

A solution of bromide 8 (1.7 g, 7.42 mmol) in dry THF was added dropwise to a suspension of magnesium metal turnings (231 mg, 9.5 mmol) in dry THF (10 mL). During the addition, two drops of 1,2-dibromoethane was added to initiate the reaction and the reaction mixture was stirred at 40°-45° C. for 1-2 hrs. The solution was cooled in an ice bath and DMF (0.83 mL, 10.71 mmol) was added dropwise. The mixture was stirred for one hour and was warmed to room temperature. The reaction was quenched by careful addition of 10% $HCl_{(aq)}$ and the resulting mixture was extracted with ethyl acetate. The combined organic extracts were washed with 10% $HCl_{(aq)}$, $H_2O$, brine, then dried and concentrated to afford a yellow oil, which was purified by column chromatography ($CHCl_3$/hexane) to yield compound 9 (1.2 g, 91%). $^1$H-NMR ($CDCl_3$) $\delta$9.79 (s, 1H), 7.37 (dd, 1H, $J_{ortho}$=7.94 Hz, $J_{meta}$=1.4 Hz), 7.26 (d, 1H, $J_{meta}$=1.4 Hz), 6.84 (d, 1H, $J_{ortho}$=7.94 Hz), 1.72 (s, 6H). MS, m/e (rel. intensity): 178 (M$^+$, 51), 163 (100), 138 (20), 137 (66), 109 (7), 91 (3), 43 (10).

EXAMPLE 9

Synthesis of 3,4-O-isopropylidene-6-nitrobenzaldehyde (C)

Aldehyde 9 (800 mg, 4.49 mmol) was added dropwise with stirring to 9 mL of 55% nitric acid at 0° C. over a period of ten minutes. The reaction mixture was stirred for 1 hr. at 30°-35° C., then cooled in an ice bath, diluted with ice water (15 mL) and extracted with ethyl acetate (2×10 mL). The extracts were washed with $H_2O$ (3×5 mL), dried ($MgSO_4$) and concentrated to give the product C as a yellow solid. The crude product was purified by column chromatography (ethyl acetate/hexane) and afforded C (930 mg, 93%). $^1$H-NMR ($CDCl_3$) $\delta$10.3 (s, 1H), 7.45 (s, 1H), 7.27 (s, 1H), 1.77 (s, 6H). MS, m/e (rel. intensity):223 (M$^+$, 27), 208 (12), 193 (27), 153 (100), 134 (20), 107 (16), 79 (11), 41 (20).

EXAMPLE 10

Synthesis of 6-[$^{18}F$]FNE

Figure 4:
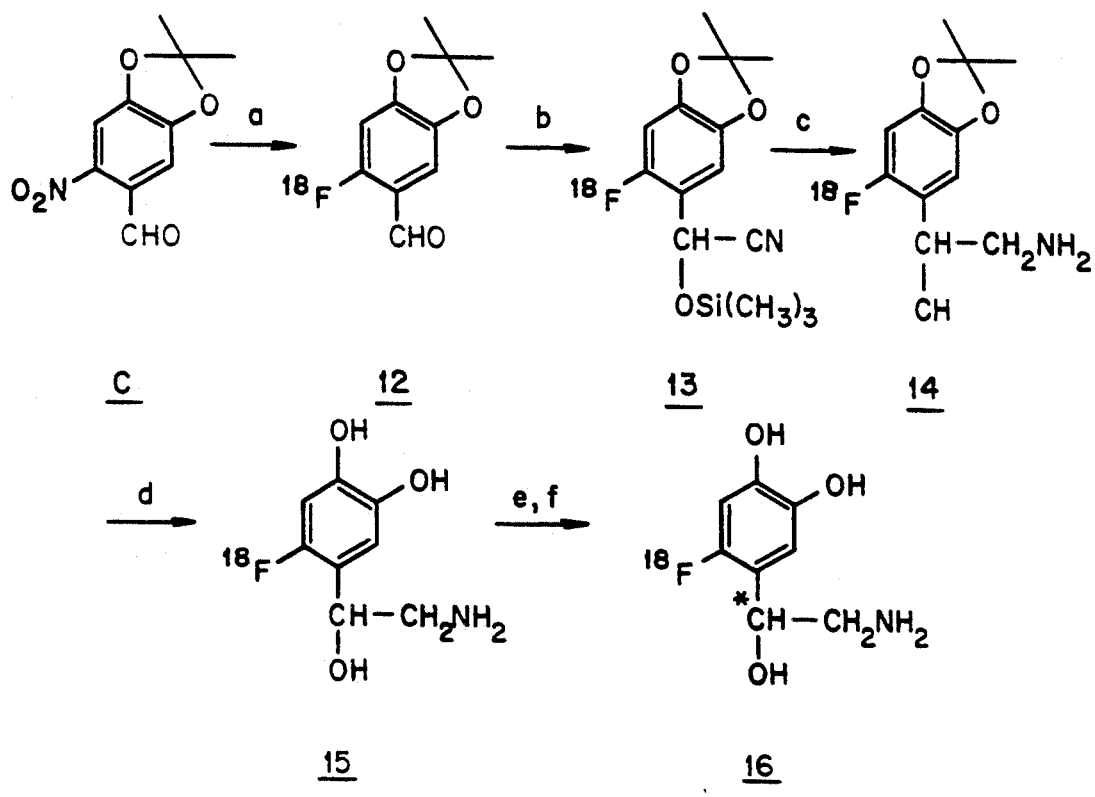
FIG. 4 illustrates the synthesis and resolution of 6-[$^{18}F$]FNE (designated as compound 16) in accordance with the present invention. Steps are as follows: (a) $K^{18}F$/Kryptofix 222; (b) $(CH_3)_3SiCN$: $ZnI_2$; (c) $LiAlH_4$; (d) HCOOH; (e) semipreparative HPLC; and (f) chiral HPLC.

The synthesis and resolution of 6-[$^{18}F$]FNE (designated as Compound 16) is shown in FIG. 4. The steps are as follows: (a) K$^{18}$F/kryptofix 222; (b) $(CH_3)_3SiCN$, $ZnI_2$; (c) $LiAlH_4$; (d) HCOOH; (e) semipreparative HPLC; and (f) chiral HPLC. A suitably protected dihydroxy aromatic substrate, 3,4-O-isopropylidene-6-nitrobenzaldehyde (C) produced as described in Example 9, was chosen as the precursor of 6-[$^{18}F$]FNE in the expectation of achieving an acceptable radiochemical yield for the substitution and easy removal of the protecting group under mild conditions. Table II shows the time taken and relative yield (corrected for decay) for each step as the synthesis progressed. Nucleophilic aromatic substitution of compound C by kryptofix/K$_2CO_3$ activated [$^{18}F$]fluoride ion in DMSO at 120° C. for 10 min gave a radiochemical yield of 40-45%. The isolated crude product 12 was converted to the corresponding cyanohydrin trimethylsilyl ether 13, followed by in situ lithium aluminum hydride reduction to give the protected dihydroxy amino alcohol 14, as described by Kirk et al., *J. Med. Chem.*, 22, 1493 (1979) the disclosure of which is incorporated by reference herein.

TABLE II

Time Elapsed and Relative Yield at Various Stages in the Radiosynthesis and Resolution of 6-[$^{18}F$]FNE

| Step Completed | Relative Yield mCi (EOB) | Total Time Min. |
|---|---|---|
| [$^{18}F$]fluoride dried at 120° C. azeotropically with $CH_3CN$ | 100 | 0 |
| fluorination at 120° C. for 10 min, crude product extracted with $CH_2Cl_2$ | 40 | 18 |
| cyanohydrin formation at room temperature for 10 min, solvent evaporated under | 32 | 40 |

TABLE II-continued

Time Elapsed and Relative Yield at Various Stages in the Radiosynthesis and Resolution of 6-[$^{18}F$]FNE

| Step Completed | Relative Yield mCi (EOB) | Total Time Min. |
|---|---|---|
| vacuum reduction at 50° C. for 10 min, crude product extracted with CH$_2$Cl$_2$ | 29 | 62 |
| hydrolysis at 100° C. for 5 min, 6-[$^{18}F$]FNE collected from semipreparative HPLC | 20 | 93 |
| resolution on chiral HPLC, (+)- and (−)-6-[$^{18}F$]FNE collected | 6 × 2 | 128 |

Quantitative yields were obtained for both steps. The product was hydrolyzed with 88% formic acid in a closed vessel (fitted with a 0.2-mm tube to release pressure) at 120° C. for 7 min. 6-Nitropiperonal was also examined as a precursor in the synthesis of 6-FNE and although it gave a higher radio-chemical yield for the substitution step (51% vs. 42%), harsh conditions (heating with strong acid for longer time) were required for the hydrolysis, resulting in decomposition and by product formation.

More specifically, the synthesis was carried out as follows:

10(A) Preparation of 3,4-O-Isopropylidene-6-nitrobenzaldehyde (C). Compound 1 was prepared as described in Example 9.

10(B) Synthesis of NCA 3,4-O-Isopropylidene-6-[$^{18}F$]fluorobenzaldehyde (12). K$^{18}$F/kryptofix 222 was prepared as described in Example 1. A solution of compound C (10 mg) in 0.3 mL of dry DMSO was added to the dried K$^{18}$F/kryptofix 222. The mixture was stirred at 120° C. for 10 minutes, quenched by addition of water (3 mL), and then extracted with CH$_2$Cl$_2$ (2×3 mL). The CH$_2$Cl$_2$ extracts were dried by passing them through a K$_2$CO$_3$ column, concentrated, and used directly in the synthesis of compound 14. The crude product compound 12 was analyzed by thin-layer chromatography (TLC) (silica, 7:3 hexane/ethyl acetate, R$_f$=0.65).

10(C) Synthesis of NCA 3,4-O-Isopropylidene-6-[$^{18}F$]fluorophenethanolamine (14). To the residue containing compound 12 were added 0.3 mL of trimethylsilyl cyanide and approximately 5 mg of zinc iodide. The mixture was stirred at room temperature for 10 minutes. The excess trimethylsilyl cyanide was then removed in vacuo. The residue was cooled in an ice bath, followed by sequential addition of 0.3 mL of anhydrous ether and 0.5 mL of 1M lithium aluminum hydride. After refluxing at 50° C. for 10 minutes, the reaction mixture was cooled in ice and the excess hydride was decomposed by the sequential addition of 0.1 mL of 20% NaOH and 2 mL of H$_2$O. The resulting mixture was stirred for 1 minute and extracted with CH$_2$Cl$_2$ (2×3 mL). Cyanohydrin trimethylsilyl ether (compound 13) an phenethanolamine (compound 14) had R$_f$ values of 0.73 and 0.04, respectively, on TLC (silica, 7:3 hexane/ethyl acetate). The HPLC analysis of compound 4 was performed on a Phenomenex ODS 2 column (CH$_3$CN/H$_2$O=90:10, 0.8 mL/min, 254 nm, retention time=3.7 min), or on a Phenomenex ODS 1 column (CH$_3$CN/0.01M KH$_2$PO$_4$=65:35, 0.8 mL/min, 254 nm, retention time=9 min).

10(D) Synthesis of NCA (+)-6-[$^{18}F$]FNE (15). The CH$_2$Cl$_2$ extracts containing compound 14 were evaporated under a stream of nitrogen. Formic acid (88%, 1 mL) was added to the residue, and the mixture was heated in a closed vessel (fitted with a 0.2-mm tube to release pressure) at 100° C. for 5 minutes. The solvent was evaporated and the residue was dissolved in 1.5 mL of 2.5% CH$_3$COOH. The labeled racemic 6-[$^{18}F$]FNE was purified by a semipreparative HPLC (Phenomenex ODS1 Column, 25×1.0 cm) eluting with 2.5% CH$_3$COOH (2.7 mL/min, 254 nm). The fraction eluting at 8 minutes was collected and concentrated by rotary evaporation. The product was identified on a Phenomenex ODS1 or ODS2 column (25×0.46 cm) under the following conditions: 2.5% CH$_3$COOH, 0.8 mL/min or CH$_3$CN/0.01M KH$_2$PO$_4$=65:35, pH 3.14, 0.8 mL/min. The radioactive peak corresponding to 6-[$^{18}F$]FNE had the same retention time as an authentic unlabeled sample which had been added as carrier. Radiochemical purity was also assayed by TLC (silica; BuOH/H$_2$O/HOAc/EtOAc=1:1:1:1) in the presence of unlabeled 6-FNE as carrier. 6-FNE was visualized with ninhydrin and radioactivity corresponded to the carrier spot (R$_f$=0.69). Radiochemical purity was 98%.

EXAMPLE 11

Resolution of Racemic 6-FNE

In principle, enantiomerically pure 6-FNE could be derived from optically active cyanohydrins, prepared through the use of chiral catalysts, as discussed by Matthews et al., *Aust. J. Chem.*, 41, 1697 (1988), and Warasaka et al., *Chem. Lett.*, 2073 (1987) enzyme-catalyzed ester cleavage, designated by Ohta et al., *Tetrahedron*, 45 5469 (1989), Waldermann, *Tetrahedron Lett.*, 30, 3057 (1989); esterification, discussed by Wang et al., *Tetrahedron Lett.*, 30 1917 (1989); or enzyme-catalyzed enantioselective addition of hydrogen cyanide to aldehydes, as described by Effenberger et al., *Tetrahedron Lett.*, 31, 1249 (1990), and Maeda et al., *Appl. Radiat. Isot.*, 41, 463 (1990). The description in each of these articles is incorporated by reference herein. However, these approaches were not suitable for the radiosynthesis of 6-[$^{18}F$]FNE, since, in addition to the poor optical yields and the long reaction times required by these processes, the rapid, sequential reduction, hydrolysis, and purification steps required for $^{18}$F-labeled radiosynthesis would result in racemized product. For these reasons resolution was carried out at the last stage of the purification using a chiral HPLC column, as follows:

11(A). Resolution of NCA (+)-6-[$^{18}F$]FNE. The residue obtained upon evaporation of solvent in Example 10(D) was dissolved in 0.5 mL of 0.02M HClO$_4$. The (+) and (−) forms of the NCA 6-[$^{18}F$]FNE were separated on an analytical scale chiral column (purchased from Daicel, Crownpak, CR(+), 15×0.46 cm). The following conditions were used: flow, 0.7 mL/min; solvent, 0.02M HClO$_4$; UV detector, 254 nm. Under these conditions the retention times for (−) and (+) -6-[$^{18}F$]FNE were 19.3 and 24.1 minutes, respectively. The total volume for each fraction was about 2 mL. Each fraction was neutralized with sterile 4.2% NaHCO$_3$ to pH 4, followed by passing through a sterile 0.22-μm filter into a sterile, pyrogen-free injection vial. Specific activity, determined by HPLC analysis (comparing the UV response of a known amount of radioactivity to a standard curve), was about 2–5 Ci/μmol (EOB).

After injecting the racemic mixture onto the chiral HPLC column, two fractions with identical amounts of radioactivity and a 5-minute difference in retention times were collected. No derivatization was necessary; the separation was efficient (separation factor $\alpha=1.33$), and the enantiomers were afforded in practical yields with a specific activity of 2–5 Ci/µmol (EOB). For example, on injection of 20 mCi of racemic 6-[$^{18}$F]FNE, 6 mCi of each enantiomer was obtained. It is important to note that the individual enantiomers of 6-FNE racemize very easily and thus care must be taken to avoid racemization. For example, evaporation of HPLC fractions containing individual enantiomers causes extensive racemization and therefore direct neutralization of the chiral HPLC fraction must be used to prepare the tracer for PET studies.

Figure 5:
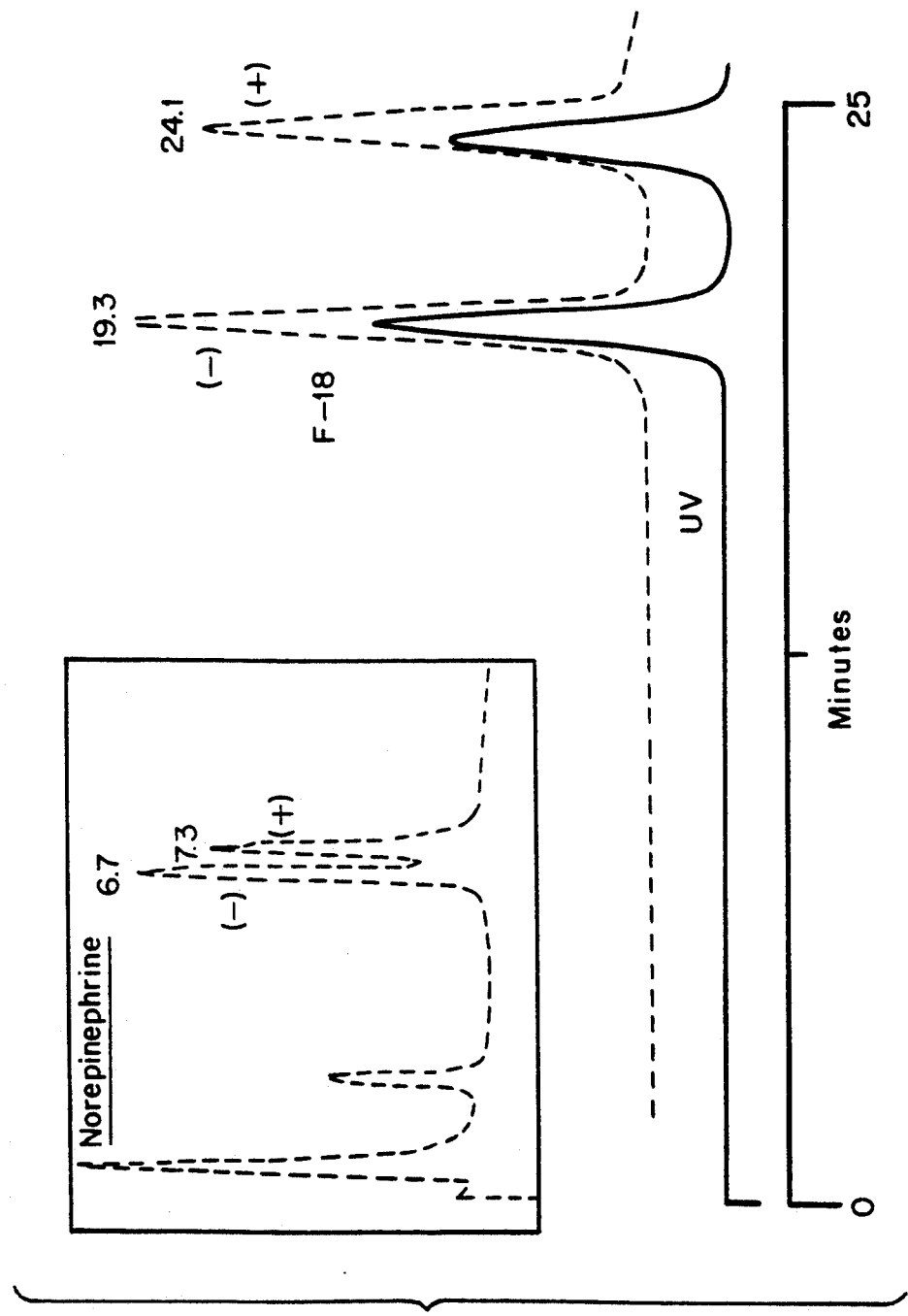
FIG. 5 is a HPLC chromatogram of the resolved enantiomers of 6-FNE obtained by coinjecting the final racemic 6-[$^{18}F$]FNE reaction mixture (dotted line) with an authentic sample of racemic 6-FNE (solid line). An HPLC chromatogram of the resolved enantiomers of NE is inserted for comparison.

FIG. 5 is a HPLC chromatogram of the resolved enantiomers of 6-FNE obtained by coinjecting the final racemic 6-[$^{18}$F]FNE reaction mixture (dotted line) with an authentic sample of racemic 6-FNE (solid line). An HPLC chromatogram of the resolved enantiomers of NE is inserted for comparison. By coinjecting the final racemic 6-[$^{18}$F]FNE reaction mixture (dotted line in FIG. 5) with an authentic sample of racemic 6-FNE (solid line in FIG. 5), an HPLC chromatogram of the resolved enantiomers was obtained. It is noteworthy that the separation factor for the enantiomers of 6-fluoronorepinephrine was significantly greater than that for the enantiomers of norepinephrine itself (1.33 vs. 1.13; the chromatogram of the resolved enantiomers of NE is inserted in FIG. 5 for comparison). The assignment of the two peaks from racemic NE was achieved by coinjecting with an authentic sample of (−)-NE. The first peak (retention time 6.7 minutes) corresponded to (−)-NE, and therefore the second peak (retention time 7.3 minutes) corresponded to (+)-NE.

EXAMPLE 12

Peak Assignment of Resolved 6-FNE Enantiomers

Chiral HPLC peak assignment for the resolved enantiomers of racemic 6-FNE was performed by using two independent methods: (1) polarimetric determination, and (2) reaction with dopamine β-hydroxylase. The resolved enantiomers obtained from the chiral HPLC column in Example 11 (max 0.1 mg per injection to obtain baseline resolution) were neutralized and carefully concentrated to a small volume. A sample of the enantiomer having the shorter retention time was submitted for optical rotation analysis (Rudolph Instruments, Inc.) Although the concentration of the sample was too low to give a quantitative value for the optical rotation which could be used to calculate an absolute rotation with the polarimeter system used, the results consistently indicated the substance to be levorotatory. Thus, while this system has proven ideal for the rapid efficient resolution of NCA 6-[$^{18}$F]FNE in practical yields for PET studies, the small capacity of the chiral column and the ease of racemization precluded preparation of larger quantities of resolved 6-FNE.

Dopamine β-hydroxylase is known to enantiospecifically convert dopamine to (−)-norepinephrine, as discussed by Levin et al., *J. Biol. Chem.*, 235 2080 (1960), and Goldstein et al., *J. Biol. Chem.*, 237, 1898 (1962) the disclosure of both articles is incorporated by reference herein. Two enzyme incubations, with dopamine and 6-fluorodopamine, respectively, were performed simultaneously, as follows:

Dopamine β-Hydroxylase Reaction

12(a) Dopamine Hydroxylation. A mixture of 0.5 mg of dopamine, potassium phosphate buffer (0.3 mL, pH 5.7), 0.5M ascorbic acid (0.02 mL, pH 5.7), 1M sodium formate (0.05 mL), and dopamine β-hydroxylase solution (0.05 mL) was stirred in a closed vial at 30° C. The cap was removed and the vial was shaken periodically. An aliquot (ca. 1 µL) was withdrawn and subjected to chiral HPLC analysis as the reaction progressed. HPLC conditions were as follows: Crownpak CR (+) columns, 15×0.46 cm, 254 nm, 0.02M HClO$_4$, 0.7 mL/min. The retention times for dopamine, (−)-NE, and (+)-NE were 10.4, 6.6 and 7.3 minutes, respectively.

12(b) 6-Fluorodopamine Hydroxylation. The same procedure was used as described in 12(a), except 0.4 mg of 6-fluorodopamine, kindly provided by Dr. Kenneth Kirk at the National Institutes of Health, was used as a substrate. The retention times for 6-fluorodopamine, (−)-6FNE, and (+)-6FNE measured under the same HPLC conditions were 21.1, 18.0, and 22.6 minutes, respectively.

Figure 6:
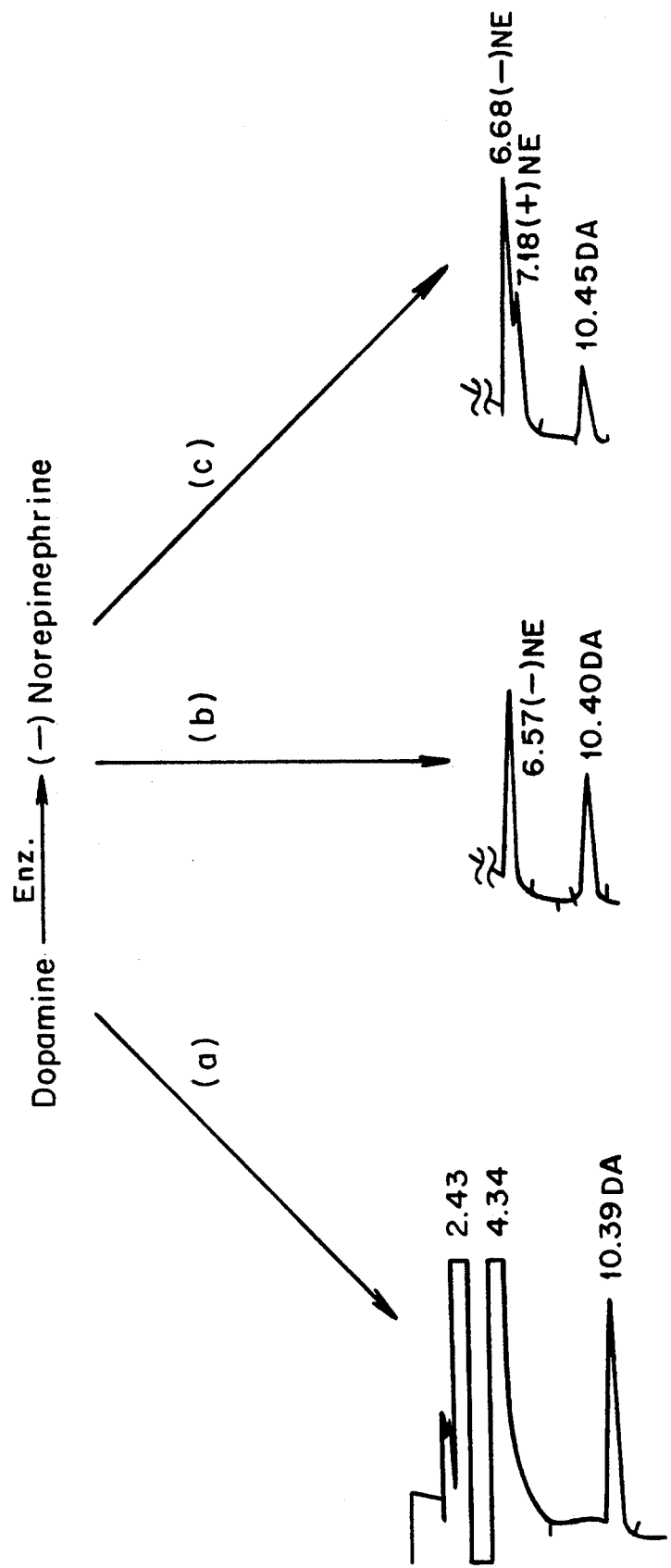
FIG. 6 shows HPLC traces of a reaction mixture resulting from the incubation of dopamine with dopamine $\beta$-hydroxylase; (a) reaction at 1 min; (b) reaction at 1 h; and (c) coinjection of b with racemic NE.
Figure 7:
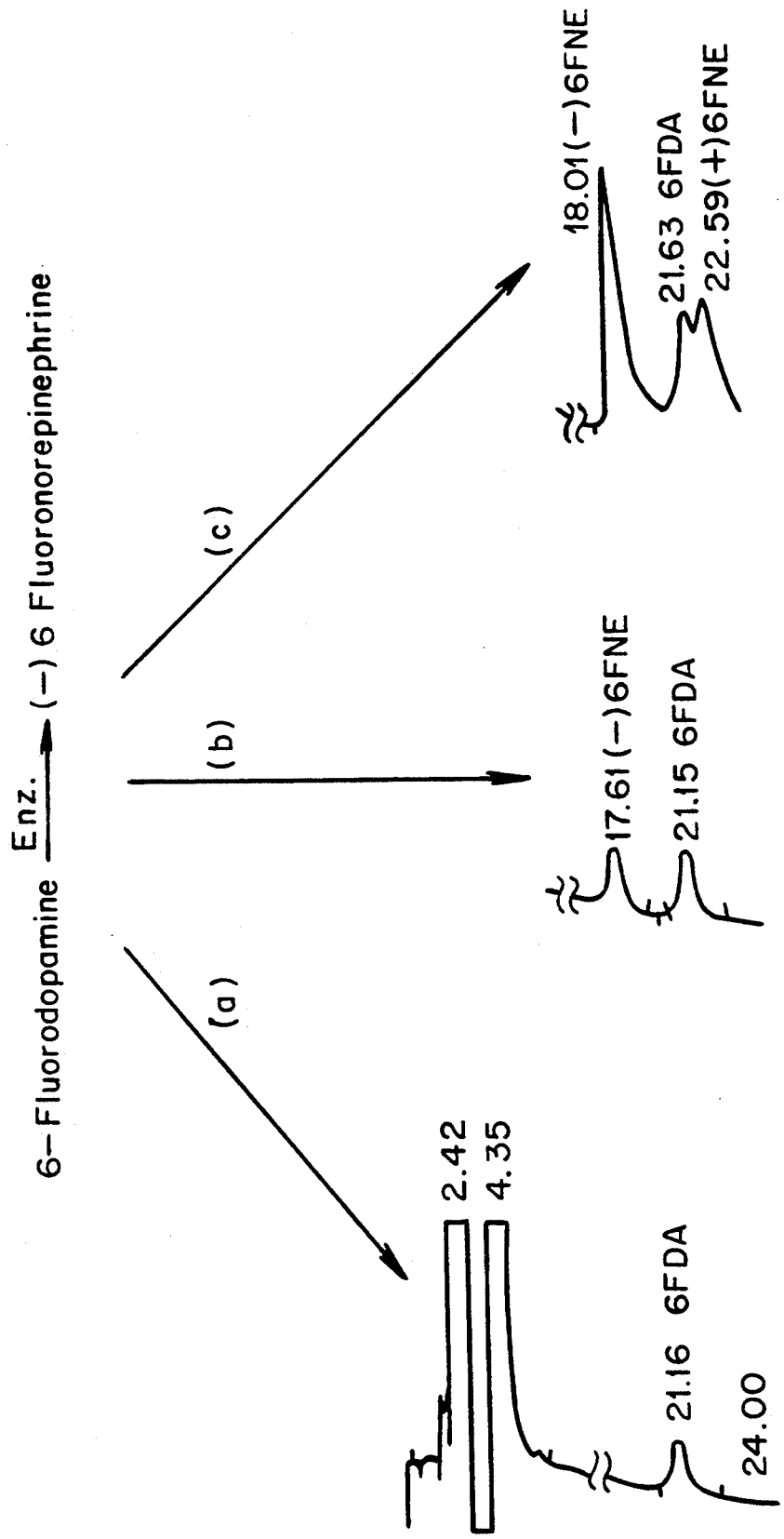
FIG. 7 shows HPLC traces of a reaction mixture resulting from the incubation of 6-fluorodopamine with dopamine $\beta$-hydroxylase; (a) reaction at 2 min; (b) reaction at 1 h and (c) coinjection of b with racemic 6-FNE.

FIG. 6 shows HPLC traces of a reaction mixture resulting from the incubation of dopamine with dopamine β-hydroxylase; (a) reaction at 1 min; (b) reaction at 1 h; and (c) coinjection of b with racemic NE. In less than 1 hour, a peak corresponding to (−)-NE (retention time 6.7 minutes) appeared when the enzyme mixture which contained dopamine as substrate was injected onto a chiral HPLC column; (+)-NE was not observed (FIG. 6). FIG. 7 shows HPLC traces of a reaction mixture resulting from the incubation of 6-fluorodopamine with dopamine β-hydroxylase: (a) reaction at 2 min; (b) reaction at 1 h; and (c) coinjection of b with racemic 6-FNE. An analogous result was obtained when 6-fluorodopamine was used as a substrate; a new HPLC peak at 18 minutes appeared (FIG. 7). Thus UV peak coeluted with the first radioactive peak collected from 6-[$^{18}$F]FNE. Thus the levorotatory isomers of both NE and 6-FNE elute before their respective dextrorotatory enantiomers. This order of elution was also recently reported by Maeda et al., *Appl. Radiat. Isot.*, 41, 463 (1990) the disclosure of which is incorporated by reference herein, for [$^{11}$C]octopamine enantiomers when a Crownpak CR(+) HPLC column was used.

EXAMPLE 13

PET Studies of 6-[$^{18}$F]FNE In Baboons

Figure 8:
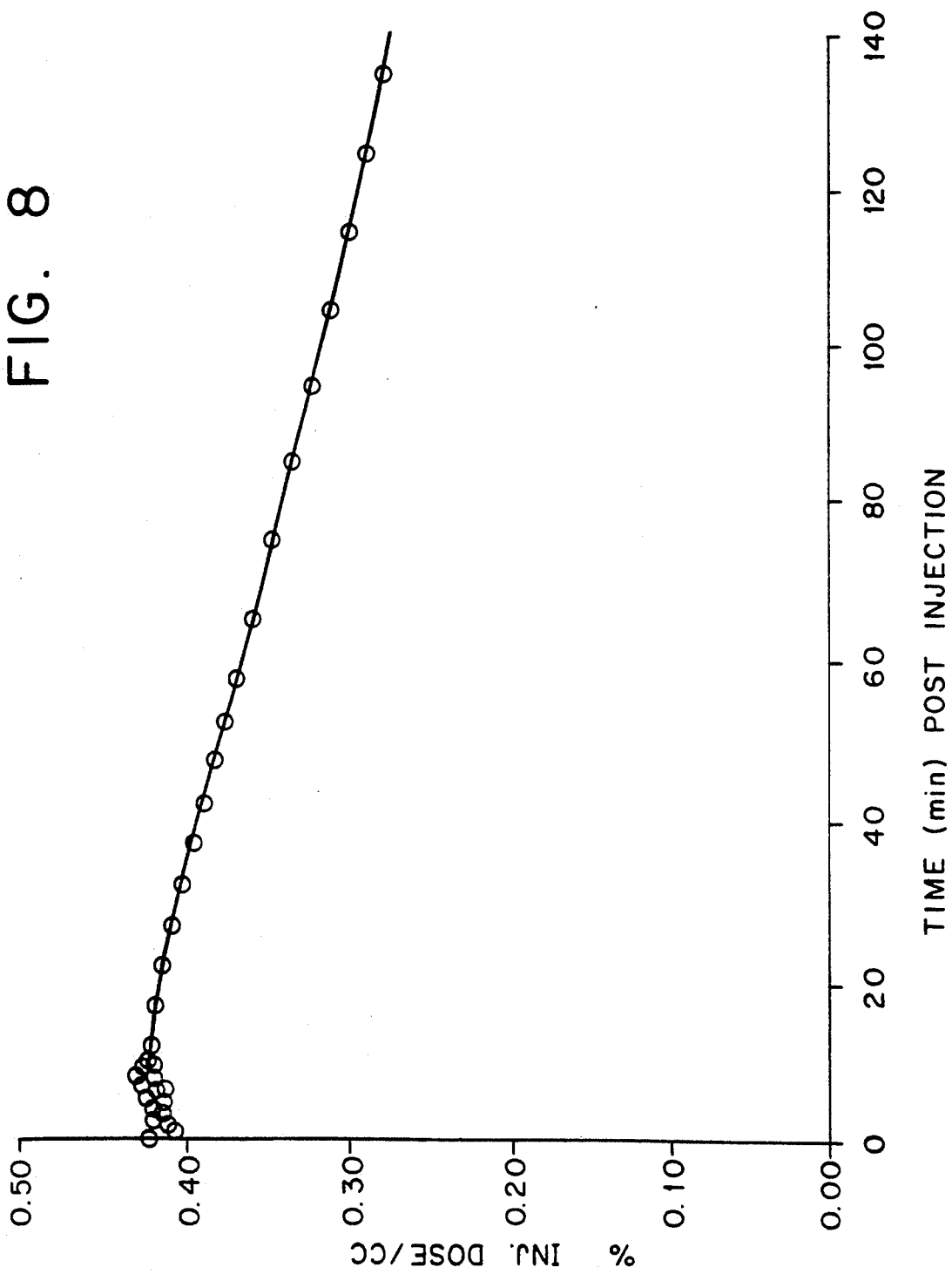
FIG. 8 is a time-activity curve for F-18 in the baboon mycocardium (left ventricular wall and septum) after injection of 5 mCi of racemic 6-[$^{18}F$]FNE.
Figure 9:
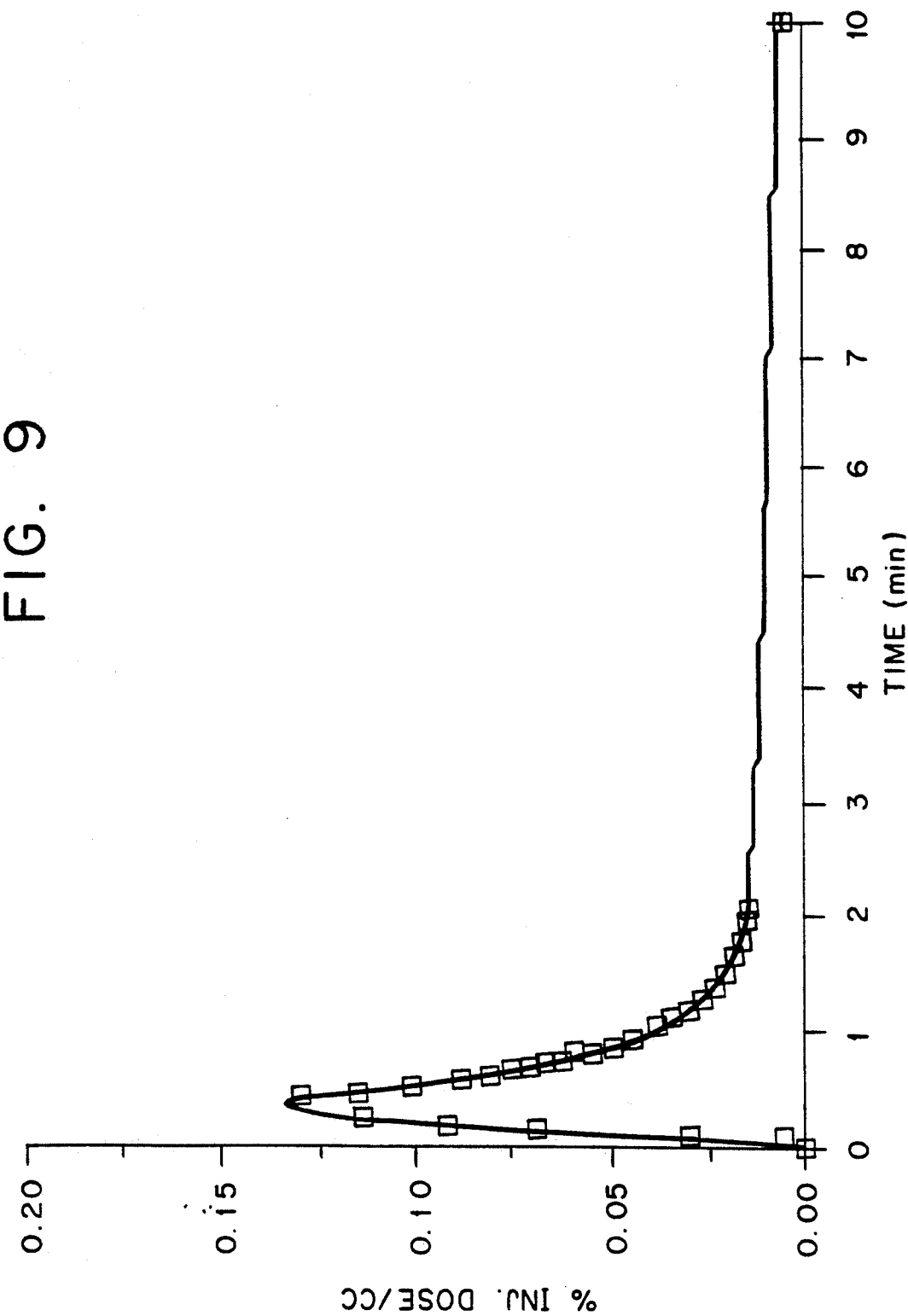
FIG. 9 is a graph showing plasma clearance of F-18 in the baboon after injection of racemic 6-[$^{18}F$]FNE.

PET studies in female baboons (*Papio anubis*) showed high uptake and retention of F-18 in the mycardium (as shown in FIG. 8) and rapid clearance from blood (as shown in FIG. 9) after the injection of racemic 6-[$^{18}$F]FNE. FIG. 8 is a time-activity curve for F-18 in the baboon mycocardium (left ventricular wall and septum) after injection of 5 mCi of racemic 6-[$^{18}$F]FNE. FIG. 9 is a graph showing plasma clearance of F-18 in the baboon after injection of racemic 6-[$^{18}$F]FNE. A peak concentration of 0.042% of the injected does/cc was observed at 10 minutes post injection. Radioactivity remained at 0.032% of the peak activity by 120 minutes post injection. The ratio of myocardium to plasma was 7 at 5 minutes and 11.2 at 135 minutes. The experiment was carried out as follows:

Adult female baboons were anesthetized and prepared for PET studies as described by Dewey et al., *Synapse*, 5, 213 (1990) the description of which is incorporated by reference herein. A solution of racemic 6-[$^{18}$F]FNE (5 mCi, 0.4 µg) in 3 mL of saline was injected intravenously. Scanning was performed for 140 minutes in a Computer Technology Imaging (CTI) positron tomograph (model 931-08/12; 15 slice, 6.5-mm slice thickness, full width at half maximum (FWHM) with an in-plane resolution of 6.0×6.0 mm (FWHM). The following scanning protocol was used: ten 30-s scans, followed by five 60-s scans, followed by ten 5-minute scans, followed by eight 10-minute scans. In every case, an initial transmission scan was performed 2.0 minutes prior to radiotracer injection in order to determine the proper position of the animal in the gantry. Upon completion of this scan, adjustments in position were made as necessary and a regular transmission scan (10 minutes) was performed in order to correct for the attenuation of the annihilation photons. The tomograph was cross calibrated with the well-counter used for the measurement of radioactivity in the plasma samples. A rectilinear scan was performed by placing the baboon's head in the gantry and moving through the rostral caudal extent of the animal (10-mm increments) to include the bladder at the most caudal level. Scanning was performed for 1.5 minutes at each position. Vital signs including heart and respiratory rate were monitored and recorded throughout the length of the study.

The time-activity curve for F-18 after the injection of 6-[$^{18}$F]FNE was generated from a region of interest over the left ventricular wall and the septum. Immediately following completion of the dynamic acquisition, a rectilinear scan (qualitative) was performed beginning at the head and continuing throughout the rostral-caudal extent of the trunk. Radioactivity was distributed in the parotid glands, the heart, liver, and bladder (data not shown). There was no change in vital signs at any time during the study.

Thus, while we have described what are the presently contemplated preferred embodiments of the present invention, other and further changes and modifications could be made thereto without departing from the scope of the invention, and it is intended by the inventors to claim all such changes and modifications.

We claim:

1. A method for synthesizing a no-carrier-added (NCA) aryl [$^{18}$F]fluoride selected from the group consisting of 6-[$^{18}$F]fluoro-L-DOPA, 2-[$^{18}$F]fluorotyrosine, 6-[$^{18}$F]fluoronorepinephrine, and 6-[$^{18}$F]fluorodopamine, comprising reacting the corresponding aromatic nitro compound having a suitably protected hydroxyl substituent on an electron rich ring of the aromatic nitro compound with a no-carrier added (NCA) [$^{18}$F]fluoride ion.

2. A method according to claim 1, wherein said synthesis results in said aryl [$^{18}$F]fluoride composition having a specific activity of from about 2 Ci/$\mu$mole to a specific activity of about 10 Ci/$\mu$mole.

3. A method according to claim 1, wherein said fluoride composition includes a catechol moiety on said electron rich ring.

* * * * *